United States Patent [19]  [11] 4,251,159
White  [45] Feb. 17, 1981

[54] DISPOSABLE MULTI-CHAMBER CUVETTE
[75] Inventor: Fred K. White, Miami, Fla.
[73] Assignee: American Hospital Supply Corporation, Evanston, Ill.
[21] Appl. No.: 3,503
[22] Filed: Jan. 15, 1979
[51] Int. Cl.³ .............................................. G01N 1/10
[52] U.S. Cl. ..................................... 356/246; 422/58
[58] Field of Search ............... 356/197, 208, 240, 246; 422/58; 250/432 R

[56] References Cited
U.S. PATENT DOCUMENTS

| 3,718,439 | 2/1973 | Rosse et al. | 356/246 |
| 3,759,374 | 9/1973 | Helger et al. | 356/246 X |

FOREIGN PATENT DOCUMENTS 2435317  2/1976  Fed. Rep. of Germany ........... 356/246

Primary Examiner—Conrad J. Clark
Assistant Examiner—Bruce Y. Arnold
Attorney, Agent, or Firm—Tilton, Fallon, Lungmus & Chestnut

[57] ABSTRACT

A disposable multi-chamber cuvette for use with photometric chemical analyzers. Each chamber is defined by an individual cup formed of optically-clear plastic material having its own side, end, and bottom walls. Each pair of adjacent cups are joined by a thin vertical web that is spaced inwardly from the side walls of adjacent cups so that light piping between cups is minimized. The thin webs preferably extend along the longitudinal vertical midplane of the series. A unitary cover seals the open tops of the cups and coacts to rigidify the entire assembly. A suitable handle projects from one end of the series to provide means for inserting and removing the rigid cuvette cartridge into and from a chemical analyzer.

20 Claims, 5 Drawing Figures

DISPOSABLE MULTI-CHAMBER CUVETTE

BACKGROUND

U.S. Pat. No. 3,718,439 discloses a photometric instrument of a type in common use for performing clinical chemical diagnostic analyses. The patent also shows and describes a three-chambered plastic cuvette for use in such an instrument, the cuvette including a pair of planar side walls, two end walls, and two partitions or barrier walls which divide the interior of the cuvette into three separate compartments. The result is a rigid cuvette structure which may be readily inserted into the instrument for the performance and recording of any of a variety of diagnostic tests. For example, where the test is one which utilizes a standard mode, such as a serum glucose test, all three compartments of the cuvette would contain a liquid reagent. As is well known, a laboratory technician would add measured amounts of a serum standard and a patient's serum, respectively, to two of the compartments, the third compartment having nother further added to it and serving merely as a blank. Optical density of the solution in each chamber is then measured automatically by projecting a beam of light therethrough and comparing the intensity of the transmitted light to the incident light, such optical density being representative of the concentration of the solution.

Measurement precision requires that the light impinging on the detector consist of light transmitted through the solution, in contrast to light which might reach the detector by any other route. If the material of the cuvette serves as a light pipe, then it is believed apparent that the accuracy of the test results may be adversely affected because of light reaching the detector via a route other than through the solution being tested. Thus, should light be piped from the chamber undergoing examination into an adjacent chamber, at least a fraction of that diverted light may be scattered by the contents of the adjacent chamber back into the original chamber, or possibly even directly to the detector, to adversely affect the test results. The detector would necessarily be sensing the light transmission characteristics of the contents of more than one chamber at the same time; even in the unlikely event that the contents of the successive chambers were the same, the readings would lack uniformity because a test on the contents of the middle chamber would be affected by scattered light from both end chambers whereas a test involving an end chamber would be affected by scattered light from only one side.

Such undesirable light piping effects might be reduced by treating the internal surfaces of a cuvette so that light striking the barrier walls between chambers would be blocked from entering and returning from adjacent chambers and, in actual practice, the walls (particularly the "barrier" walls) of commercial versions of the cuvette disclosed in U.S. Pat. No. 3,718,439 are etched or frosted to reduce objectionable light transmission through the walls so treated. A major disadvantage of such treatment is that it is a relatively expensive procedure in the production of a product intended for use as a disposable item. While a lower cost solution to the problem of light piping has long been needed, no such solution in a multi-chambered cuvette having sufficient rigidity and optical properties to serve as a unitary disposable cartridge has heretofore appeared.

Other patents indicative of the state of the art are U.S. Pat. Nos. 3,520,659, 3,697,227, 3,532,470, 3,540,857, 3,582,283, 3,582,285, 3,545,934, 3,554,705, 3,477,821, 3,497,320, and 3,477,822.

Summary

A main object of this invention lies in providing an improved cuvette which overcomes or greatly reduces the aforementioned problems; that is, a cuvette which has multiple chambers, is rigid enough to be handled and used as a unitary cartridge, has superior resistance to light piping effects, provides excellent optical properties, and is nevertheless relatively inexpensive to produce. Lower production costs are achieved in large part by applicant's discovery of an improved cuvette construction which eliminates the need for frosting or otherwise treating the inside surfaces of a multi-chambered cuvette for the purpose of eliminating objectionable light piping.

Briefly, the cuvette takes the form of a plurality of optically-clear (i.e., non-frosted) cups, such cups each having side, bottom, and end walls and being arranged in a longitudinal series with the end walls of successive cups disposed in spaced-apart relation. Rigidity is achieved by joining the cups with narrow vertical webs formed integrally with such cups and extending at substantially right angles to the end walls thereof, and by a horizontal cover which seals the upper ends of the cups and which also prevents flexing and possible fracture of the narrow webs. The webs and cover therefore coact with the cups to produce a rigid unitary multi-chambered cuvette. Because the webs extend at right angles to the end walls, are relatively narrow, and terminate a substantial distance above the bottoms of the cups, no objectionable piping of light occurs from one chamber to the next notwithstanding the fact that such webs are themselves transparent and formed integrally with the cups.

In the preferred embodiment disclosed, the cuvette has its interconnecting webs extending along the longitudinal vertical midplane of the series of cups. Each web has a thickness no greater than about 25 percent of the width of the end walls; preferably, such web thickness would fall within the range of about 10 to 20 percent of the width of each such end wall. The side and end walls of each cup are planar with the side walls preferably tapering gradually downwardly and inwardly. The cuvette includes an integral supporting handle which projects from one end of the series of cups and, in the marketed form of the cuvette, at least certain of the cups would have selected chemical reagents sealed therein.

Other features, objects, and advantages of the invention will become apparent from the specification and drawings.

Drawings

Description

Figure 1:
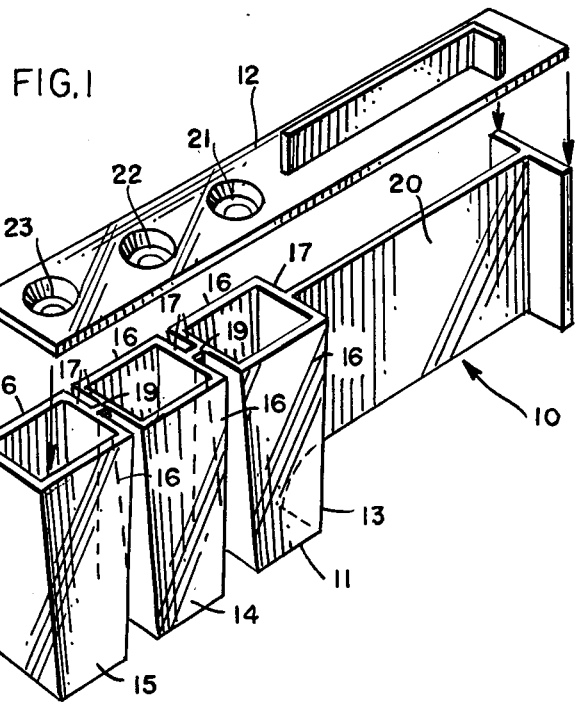
FIG. 1 is an exploded perspective view of a cuvette embodying the present invention.

Referring to the drawings, the numeral 10 designates a multi-chambered cuvette having a lower body section 11 and a cover or top section 12. Body section 11 has a plurality of open-topped cups 13, 14, and 15, each cup having its own side walls 16, end walls 17, and bottom wall 18. In the illustration given, all of such walls are planar and the side walls 16 taper downwardly and inwardly; however, it is to be understood that the tapered configuration is important primarily to facilitate molding and that the bottom wall, and possibly other walls of each cup, need not be planar.

Figure 2:
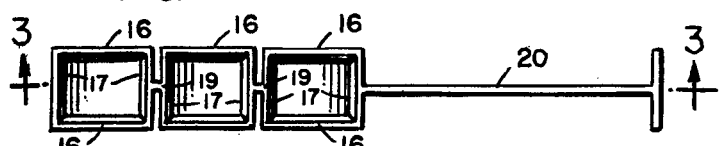
FIG. 2 is a top plan view of the body section of the cuvette.

Cups 13–15 are arranged in a longitudinal series with the end walls of adjacent cups spaced apart as shown most clearly in FIGS. 1 and 2. Narrow webs or ribs 19 extend between the opposing end walls 17 of adjacent cups. The webs are disposed at substantially right angles to the end walls and, in the embodiment illustrated, such webs extend along the longitudinal vertical midplane of the series of cups. Webs 19 are relatively thin and, in the absence of cover 12, are insufficient to withstand moderate forces tending to twist or pivot one cup with respect to another. For example, one holding such a cuvette body (i.e., without cover 12) in his hands might easily bend one cup relative to another to flex and/or fracture the rib connecting the two. Each of the ribs should be relatively narrow or thin—that is, it should have a thickness no greater than about 25 percent of the width of each of the end walls 17. It is believed that ideally such thickness should fall within the range of about 10 to 20 percent of the width of each end wall.

Figure 3:
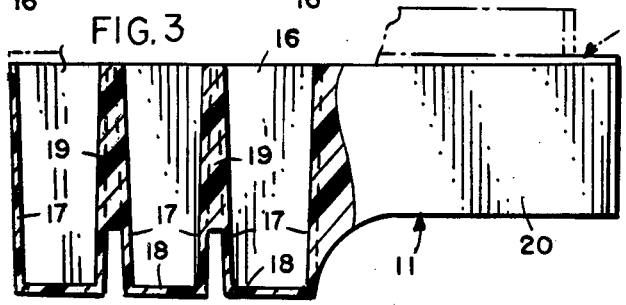
FIG. 3 is a side elevational view of the body section.

Referring to FIG. 3, it will be noted that each rib 19 terminates a substantial distance above the bottom walls of the adjacent cups. Such a relationship contributes in eliminating objectionable light conduction between successive chambers, especially with respect to those portions of the chambers (the lower third of side walls 16) through which light is beamed during photometric analysis.

Body 11 also includes a supporting handle 20 which projects outwardly from one end of the series of cups. The handle therefore extends along the longitudinal vertical midplane of the body in general alignment with webs 19. While a particular handle configuration is illustrated, it is to be understood that such configuration may be modified considerably to suit the preferences and requirements of use. The primary purpose of handle 20 is to provide a means for conveniently gripping the cuvette for manual insertion into and removal from a photometric chemical analyzer such as, for example, an analyzer of the type disclosed in U.S. Pat. No. 3,718,439.

The entire body 11 is integrally formed from the same material, preferably a polymeric material such as an acrylic, a polycarbonate, or a polyolefin. An acrylic polymer is believed preferable because of its excellent optical properties, chemical resistance, and availability; however, other materials having similar properties may be used. A particularly important aspect of the invention is that the entire body, and particularly side walls 16 and end walls 17 of each cup, as well as connecting webs 19, may be optically clear. No frosting of surfaces or other special treatment thereof to prevent light transmission is required.

Cover 12 extends horizontally and longitudinally and is secured by sonic welding, solvent bonding, or any other suitable means to body 11. When so secured in place, the cover seals the chambers of all of the cups 13–15. Depending on the type of clinical test to be performed, some or all of the sealed cups would be supplied with one or more reagents (not shown) disposed therein. For example, if the cuvette were to be used in conducting a serum glucose test, all three cups would contain an appropriate liquid reagent such as a dilute solution of orthotoluidine in glacial acetic acid.

Above each cup, cover 12 is provided with a frangible or pierceable section 21–23. An upstanding L-shaped rib or flag 24 projects from the upper surface of cover 12 and is dimensioned and shaped to control the duration and temperature of the incubation step when the cuvette is inserted into an analyzer, all as described in U.S. Pat. No. 3,718,439.

As already indicated, the cover 12 and ribs 19 extend along planes at right angles to each other and coact to provide sufficient rigidity for the cuvette assembly so that it may be easily manipulated in laboratory operations and, in particular, may be readily inserted into, supported within, and removed from a photometric chemical analyzer. Such structural rigidity is achieved without problems of light piping in use, notwithstanding the fact that the body 11 of the cuvette (and also the cover 12, if desired) is transparent or optically clear.

Figure 5:
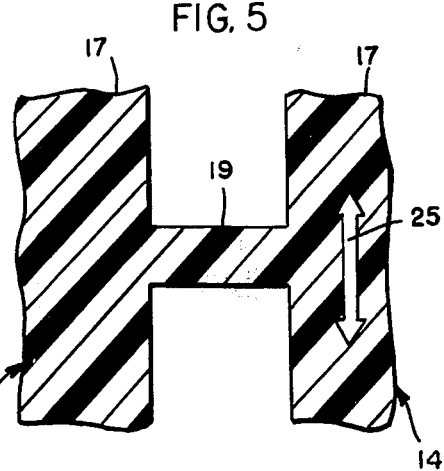
FIG. 5 is a greatly enlarged horizontal sectional view of that portion of the cuvette encircled by phantom lines in FIG. 4.

FIG. 5 somewhat schematically depicts one reason why objectionable light piping between adjacent cups does not occur. As a beam of monochromatic light is directed through opposite side walls 16 of a cup (or as parallel beams are similarly and simultaneously directed through two or more cups), some of the light is absorbed by the liquid contents within the cup and some of it also illuminates the side and end walls of that cup. Should the beam be projected through cup 14, for example, the light that would be piped by the walls of that cup would be transmitted primarily in the plane of such walls. Thus, the light transmitted by end wall 17 of cup 14 would tend to travel in the plane indicated by arrow 25 rather than travel at right angles through web 19. Because light tends to travel in straight lines and because of the limited dimensions of web 19, light passing through one cup and its contents will not produce any appreciable illumination of the contents of an adjacent cup. Consequently, a detector receiving light transmitted through one cup of the cuvette will be relatively unaffected by the undesired illumination and backscattering of such light from the contents of an adjacent cup, nor will there be any significant effect on the optical density measurements.

While the plural-chambered cuvette depicted and described herein has three cups 13–15, suitable for receiving a specimen, a standard, and a blank for conducting a single diagnostic test, it is to be understood that the number of cups might be increased (as where several photometric measurements are to be undertaken simultaneously) or even reduced (the "blank" chamber would not be needed, for example, where the test is to be performed in an absolute mode or rate mode). It will also be understood by those skilled in the art that while I have disclosed an embodiment of the invention in considerable detail for purposes of illustration, many of these details may be varied without departing from the spirit and scope of the invention.

I claim:

1. A cuvette for use in photometric chemical analyzers, comprising a plurality of optically-clear open-topped cups each having side, bottom, and end walls; said cups being arranged in a longitudinal series with the end walls of adjacent cups being disposed in spaced-apart relation; said end walls of each pair of adjacent cups being joined by a thin vertical web formed integrally with said cups; each web being spaced inwardly from said side walls of said adjacent cups and extending at substantially right angles to said end walls of said adjacent cups.

2. The cuvette of claim 1 in which said webs extend along the longitudinal vertical midplane of said series of cups.

3. The cuvette of claim 2 in which each of said webs has vertical dimensions substantially less than those of said cups.

4. The cuvette of claim 3 in which each of said webs has a lower edge terminating a substantial distance above the bottom walls of said cups.

5. The cuvette of claim 1 in which said side and end walls of said cups are planar.

6. The cuvette of claim 5 in which the width of the side walls of each cup tapers downwardly.

7. The cuvette of claim 1 in which all of said open-topped cups are sealed at the upper ends thereof by a unitary cover.

8. The cuvette of claim 7 in which chemical reagents are sealed within at least certain of said cups.

9. The cuvette of claim 1 in which an integral supporting handle projects from one end of said series of cups.

10. A cuvette for use in photometric chemical analyzers, comprising a plurality of optically-clear open-topped cups each having side, bottom, and end walls; said cups being arranged in a longitudinal series with the end walls of adjacent cups being disposed in spaced-apart relation; said ends walls of each pair of adjacent cups being joined by a thin vertical web formed integrally with said cups and extending at substantially right angles to said end walls; each of said webs extending along the longitudinal vertical midplane of said series of cups and having a thickness no greater than about 25 percent of the thickness of each of said end walls.

11. The cuvette of claim 10 in which each of said webs has a thickness within the range of 10 to 20 percent of the thickness of each of said end walls.

12. A cuvette for use in photometric chemical analyzers, comprising a body section and a cover section; said body section including a plurality of optically-clear open-topped cups each having side, bottom, and end walls; said cups being arranged in a longitudinal series with the end walls of adjacent cups being disposed in spaced-apart relation; said side and end walls of said cups being planar and said end walls of each pair of adjacent cups being joined by a thin vertical web formed integrally with said cups; each web being spaced inwardly from said side walls of said adjacent cups and extending at substantially right angles to said end walls of said adjacent cups; said cover section extending horizontally and being secured to said cups to seal the open upper ends thereof.

13. The cuvette of claim 12 in which said webs extend along the longitudinal vertical midplane of said series or cups.

14. The cuvette of claim 13 in which each of said webs has a thickness within the range of 10 to 20 percent of the thickness of each of said end walls.

15. The cuvette of claim 12 in which each of said webs has vertical dimensions substantially less than those of said cups.

16. The cuvette of claim 15 in which each of said webs has a lower edge terminating a substantial distance above the bottom walls of said cups.

17. The cuvette of claim 16 in which the width of the side walls of each cup tapers downwardly.

18. The cuvette of claim 17 in which chemical reagents are sealed within at least certain of said cups.

19. The cuvette of claim 12 in which an integral supporting handle projects from one end of said series of cups.

20. A cuvette for use in photometric chemical analyzers, comprising a body section and a cover section; said body section including a plurality of optically-clear open-topped cups each having side, bottom, and end walls; said cups being arranged in a longitudinal series with the end walls of adjacent cups being disposed in spaced-apart relation; said side and end walls of said cups being planar and said end walls of each pair of adjacent cups being joined by a thin vertical web formed integrally with said cups and extending at substantially right angles to said end walls; said cover section extending horizontally and being secured to said cups to seal the open upper ends thereof; each of said webs extending along the longitudinal vertical midplane of said series of cups and having a thickness no greater than about 25 percent of the thickness of each of said end walls.

* * * * *

UNITED STATES PATENT AND TRADEMARK OFFICE
CERTIFICATE OF CORRECTION

PATENT NO. : 4,251,159

DATED : February 17, 1981

INVENTOR(S) : Fred K. White

It is certified that error appears in the above-identified patent and that said Letters Patent are hereby corrected as shown below:

Column 3, lines 33 and 35, cancel "width" and substitute
-- thickness --.

Figure 4:
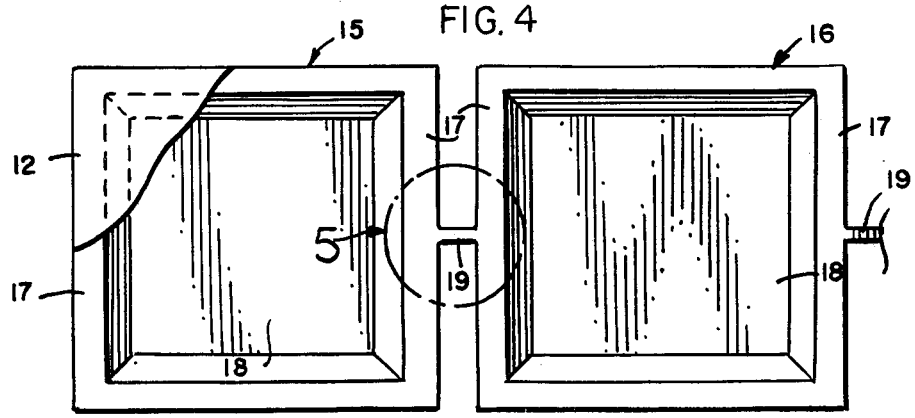
FIG. 4 is an enlarged top plan view of a portion of the cuvette with the cover broken away to reveal the relationship of a pair of adjacent cups.

Figure 4, cancel reference numeral "16" and substitute
-- 14 --.

Signed and Sealed this

Third Day of November 1981

[SEAL]

Attest:

Attesting Officer

GERALD J. MOSSINGHOFF

Commissioner of Patents and Trademarks